United States Patent [19]
Mullon et al.

[11] Patent Number: 5,795,711
[45] Date of Patent: Aug. 18, 1998

[54] CRYOPRESERVED HEPATOCYTES AND HIGH VIABILITY AND METABOLIC ACTIVITY

[75] Inventors: Claudy Jean-Paul Mullon, Framingham; Shawn Paul Cain, N. Chelmsford; Timothy Jon Perlman, Lexington, all of Mass.; Hugo O. Jauregui, Providence, R.I.; Sharda Naik; Henry A. Santangini, both of Cranston, R.I.; Donna M. Trenkler, Greene, R.I.

[73] Assignee: Circe Biomedical, Inc., Lexington, Mass.

[21] Appl. No.: 627,446

[22] Filed: Apr. 4, 1996

[51] Int. Cl.⁶ .................................................. A01N 1/02
[52] U.S. Cl. ...................... 435/1.1; 435/1.3; 435/325; 435/370; 435/374
[58] Field of Search ........................... 435/1.1, 1.3, 325, 435/370, 374

[56] References Cited

PUBLICATIONS

Kasai et al. "Large–Scale Cryopreservation of Isolated Dog Hepatocytes" *Cryobiology*, vol. 30 (1993), pp. 1–11.

*Primary Examiner*—Jeffrey Stucker
*Attorney, Agent, or Firm*—Law Office of Margit Maus

[57] ABSTRACT

An artificial liver support system is described herein which comprises cryopreserved hepatocytes having an initial viability of 80–99% and a metabolic activity 50–80% of fresh hepatocytes. Further disclosed are hepatocytes cryopreserved by dispensing hepatocytes into freezing containers, freezing the containers from between minus 50 to minus 90 degrees Celsius, storing the containers in liquid or vapor nitrogen, thawing the cryopreserved hepatocytes when ready for use and removing residual cryoprotectant media.

31 Claims, No Drawings

CRYOPRESERVED HEPATOCYTES AND HIGH VIABILITY AND METABOLIC ACTIVITY

BACKGROUND OF THE INVENTION

The present invention relates in general to the cryopreservation of cells and more specifically to the large scale cryopreservation of porcine hepatocytes.

The liver is an essential organ for the survival of humans because it serves a variety of important functions related to macromolecular synthesis, energy generation and storage, catabolism and disposal of toxic substances and waste products of intermediary metabolism. The biochemical functions in which the liver plays a major role include the metabolism of amino acids, ammonia, proteins, carbohydrates and lipids; biochemical oxidation; and metabolism and detoxification of drugs, vitamins and hormones. Given the aforementioned, acute or chronic liver impairment, carries a poor prognosis.

Treatment for end stage acute or chronic hepatic failure may be divided into two categories, namely the use of artificial liver support systems (ALS) and orthotopic liver transplantation (OLT). ALS methods include hemoperfusion, hemodialysis, hemofiltration and plasmapheresis. Unfortunately, these methods do not improve the survival because they do not provide metabolic support.

In contrast, transplantation has a 50-90% 1 year survival rate. Unfortunately however, donor livers are in high demand but in short supply. 15-30% of patients have been reported to die before a matching donor is found.

Lastly, ALS and hepatocyte transplantation methods have been studied. Specifically, isolated hepatocytes have been investigated for use in artificial liver devices to compensate for the loss of metabolic function in the damaged liver. Hepatocyte transplantation as opposed to full liver transplantation has also been investigated as an alternative treatment modality. Both techniques to be effective however, require large scale cryopreservation of viable hepatocytes.

Shinichi Kasai and Michio Mito in "Large-Scale Cryopreservation of Isolated Dog Hepatocytes", Cryobiology 30, 1-11, 1993, describes an isolation method wherein the viability of preserved hepatocytes is 75+/-3% and the estimated recovery rate is approximately 50%. Moreover, preserved hepatocytes showed 20-50% of the metabolic activity of fresh cells as assessed by ammonia and fructose loading tests, ATP content, C-14 leucine uptake. While this technique is a beginning, it leaves much room for improvement in both yield and viability of hepatocytes.

Thus it is a primary objective of the present invention to provide for a treatment method for acute and chronic hepatic failure which provides for a high yield of viable cryopreserved hepatocytes. A further objective is to provide for a high yield of viable cryopreserved hepatocytes to allow for quality control and bioburden testing prior to use.

SUMMARY OF THE INVENTION

The aforementioned objective is met in a novel and elegant manner by providing for an artificial liver comprising hepatocytes cryopreserved by the process comprising the steps of dispensing hepatocytes into freezing containers, freezing said containers from between minus 50 to minus 90 degrees Celsius, storing said containers in liquid or vapor nitrogen, thawing said cryopreserved hepatocytes when ready for use and removing residual cryoprotectant media.

DETAILED DESCRIPTION OF THE INVENTION

The present invention contemplates use of large scale cryopreserved hepatocytes for use in ALS devices. Once the donor and product have passed all the Quality Control testing, the frozen hepatocytes may be used by the treatment facility. Shortly before use the cells are thawed and loaded into an ALS device. By way of illustration and not limitation the present invention contemplates ALS devices comprising hollow fibers, micro carriers , flat sheet membranes, etc. Specifically, the present invention contemplates cartridges. This hepatocyte loaded ALS cartridge in esssence acts as a bioartificial liver that bridges hepatic function until a donor liver becomes available for transplantation or until the patient's liver regenerates itself.

Since isolated hepatocytes only survive in culture for several days or weeks and their use in hybrid ALS devices requires longer survival, long term cryopreservation techniques are essential. In addition, long term cryopreservation offers the following advantages: allows time for bioburden, endotoxin, mycoplasma, bacteria and virus testing, allows for thorough histological examination of donor animal, improves management of product inventory and supply to customers, allows for maintenance of cell samples or archives for cell testing post treatment, improves screening of cell function prior to using the cells to treat, etc.

In very general terms the present invention discloses a cryopreservation process comprising preparing a cryoprotective medium, suspending liver cells into said medium, dispensing said hepatocytes into freezer safe containers, freezing said containers for a particular period of time under particular conditions, nitrogen, either liquid or vapor, storing said containers and thawing said cells when ready for use. Generally speaking, a cryoprotectant is a compound which is used to minimize the deleterious effects of cryopreservation such as the formation of intracellular ice during freezing. By way of illustration and not limitation mention may be made of DMSO, polyethylene glycol, amino acids, propanediol, etc. The following offers specifics for the aforementioned general process.

Hepatocyte culture media have been well described in the literature and as such comprise no part of this invention. Moreover, the present invention is not limited to any particular media. Thus by way of illustration and not limitation mention may be made of the following culture media Chee's Essential Media, Modified Eagle Media, Dulbecco's Modified Eagle Medium, Leibowitz, Waymouth, and Kreb's media, etc. as described in the Gibco, BRL Life technologies catalogue, 1993-1994.

A preferred hepatocyte culture medium is one which allows the cells to withstand the extreme temperature change encountered with liquid nitrogen storage with minimal cell degradation. By way of illustration and not limitation mention may be made of Chee's modified Essential Medium supplemented with thymidine, arginine, insulin, dexamethasone, glutamine and mammalian serum. Mammalian serum may comprise fetal bovine serum, fetal calf serum and porcine serum in concentrations ranging from 10 to 90%. This preferred medium may additionally be supplemented with DMSO ranging from about 10 to about 15%, albumin ranging from about 3.5 to about 15% and glycerol ranging from about 10 to about 20%.

The most preferred medium comprises Chee's Essential Media plus Fetal Bovine Serum, hereinafter FBS, plus Dimethyl Sulfoxide, hereinafter DMSO. More specifically the cryoprotectant medium comprises from about 5 to about 20% FBS and from about 5 to about 15% DMSO. Most preferred is a cryoprotectant medium comprising 10% FBS and 10% DMSO.

The present invention is also not dependent on any one of the well known isolating techniques. However, for illustrative purposes only, mention may be made of the following techniques outlined in the ASAIO Journal 1995; 41:155–161 and in Seglen, P. O. Preparation of isolated rat liver cells. Prescott, D. M. ed Methods in cell biology. Vol.13. New York: Academic Press; 1976: 29–83; both herein incorporated by reference.

Isolated hepatocytes are then prepared for freezing. They are dispensed into freezer resistant containers at particular densities. By way of illustration and not limitation mention may be made of the following freezing containers: vials, bags, canes, etc. Preferred are plastic bags and most preferred are Cryocyte trademark of Baxter plastic bags having a capacity ranging from about 250 to about 500 ml.

Syringe assisted dispensing into freezer bags being most preferred. In this process cells are funneled through the syringe by gravity or dispensed by gentle pressure into the bags. Once the cells are introduced into the bag, the syringe may also be advantageously used to remove excess air which later promotes the thawing process. The bags are thereafter sealed. Sealing methods may comprise mechanical aluminum seals, thermal impulse heat sealers, luer lock plugs, etc. Heat sealing being most preferred. The thus sealed containers are preferrably kept at 0–4 degrees Celsius until all the containers to be cryopreserved are filled and sealed so that they may be cryopreserved simultaneously.

A wide range of cell densities may be effectively cryopreserved using the aforementioned method, namely from about 5 to about $40 \times 10^6$ cells/ml. Volumes ranging from about 10 to about 50 mls may be preserved in 250 ml freezing containers, while from about 50 to about 150 mls may be cryopreserved in 500 ml freezing containers.

Seeding is a technique used to induce controlled crystallization or ice formation in solutions which have already been cooled below freezing. Seeding can minimize damage related to ice formation related damage and is therefore beneficial to cell viability.

The present invention contemplates any of the well known seeding methods among them mention may be made of inserting a cold metal rod into the freezing containers, introducing a blast of liquid nitrogen into the freezing containers, etc.

To ensure uniform freezing, the present invention optionally contemplates the use of freezing plates. The freezing containers are sandwiched between said freezing plates. Said plates may be manufactured from any heat conducting material such as steel, aluminum, etc. Aluminum being most preferred. Said plates again are preferrably separated by spacer means. By spacer means the present invention contemplates wedges, springs, rolls, cushions, etc. Said spacer means are preferably up to 0.25 inches thick. Said spacers may be manufactured from the same material as the plates, namely any heat conducting material such as steel, aluminum, etc. Aluminum being most preferred. Aluminum is most preferred because it is an effective heat conductor and aluminum assists in removing latent heat produced during the freezing cycle. The removal of latent heat is important because cellular damage may result from an increase in temperature during freezing. In addition, aluminum acts as a nucleation site for the seeding of external ice. This advantageously controls crystallization and prevents supercooling. In sum, use of freezer plates and spacers causes uniform release of heat for an entire lot of cells. Moreover these plates ensure that all the freezing containers in a particular lot are frozen to a uniform thickness and have uniform and reproducible thawing times. Thus while it is possible to freeze without using freezer plates and spacers, they are preferred.

Once the hepatocytes are dispensed in freezing containers, they are ready to be placed in freezers. While any freezer capable of freezing from about 4 degrees Celsius to about minus 90 degrees Celsius is contemplated, a control rate freezer is preferred.

When using a non-control rate freezer cells ranging from about 5 to about $40 \times 10^6$ cells/ml in density are placed in freezer safe containers. Said containers are thereafter stored in styrofoam boxes and placed in said freezer for from about 2 to about 24 hours. The containers are thereafter removed from the freezer and immediately quenched in liquid nitrogen for long term storage. When ready to be used, the cells are thawed in a 37–42 degree Celsius water bath and residual cryoprotectant is removed by sequential washings.

When using a control rate freezer, freezing profiles are programmed into said freezers to ensure uniform freezing. All the profiles contemplated by the present invention begin once the sample's temperature reaches minus 4 degrees Celsius. The cooling rate should be between 1–10 degrees Celsius per minute before the release of latent heat(minus 12 degrees Celsius). During the latent heat release, the chamber temperature is dropped to a rate of 25 degrees Celsius per minute until the temperature falls between minus 60 and minus 70 degrees Celsius. Once the chamber's temperature falls between minus 60 and minus 70 degrees Celsius, the chamber's temperature is immediately increased to between minus 12 and minus 20 degrees Celsius at a rate of 15 degrees Celsius per minute. Freezing rates between 1–10 degrees Celsius per minute are then utilized to reach final freezing temperatures between minus 50 and minus 90 degrees Celsius.

Preferrably the control rate freezer profile includes a blast of nitrogen that is programmed to compensate for the release of latent heat. Compensating for the release of latent heat decreases the likelihood of cellular damage during cryopreservation of the cells. This programmed cold blast also assists in synchronizing the seeding of external ice on all the freezing containers in a freezing cycle. This is particularly advantageous since the critical point of cryopreserving cells occurs during the ice formation stage. Ice formation begins at a nucleation site which can be a randomly occuring cluster of molecules in the liquid phase. The nucleated ice crystals form into an ice front which expands throughout the liquid until solidification is completed.

Thus a control rate freezer is preferred because it ensures reproducible freezing cycles and thus uniform cryopreservation. To further improve reproducability, the control rate freezer may be additionally equipped with a validator which is capable of monitoring and documenting the entire cryopreservation process thereby further ensuring uniformity and reproducability. The validator is a computer programmed temperature monitoring system with traceable and calibrated thermocouples. The thermocouples allow for further monitoring to document the chamber and sample temperature throughout the freezing cycle as well as to trigger certain portions of the freezing program. By way of illustration and not limitation mention may be made of the following thermocouples:Omega sub-mini Thermocouple and teflon covered wire, etc. Hepatocytes cryopreserved via the aforementioned profiles are highly desirable for regulatory compliance and uniform commercialization.

Once cells are frozen via the aforementioned freezer techniques, they may be placed in cryogenic storage boxes for long term storage in nitrogen storage freezers. By long term storage we mean months or years. The freezing containers may be stored in either the vapor or liquid nitrogen phase. The present invention contemplates storage at temperatures below the glass transition temperature of water or −120 degrees Celsius, where it is generally believed that biological time and activity is stopped and thus cells may be stored for years.

Prior to use, the cells must be thawed and DMSO must be removed. Thawing is accomplished via a 37–42 degree Celsius bath. The cells are removed from the container when a slush appears. The cells are then poured into a centrifuge tube containing cold culture media. The initial cell volume is diluted in the centrifuge tube by adding 5 to 10 times the initial cell volume in fresh cold culture media. The suspension is then spun down at 7–15 g for 2 to 5 minutes. The supernatant is aspirated to remove the media containing the residual DMSO. Thereafter, from about 2 to about 4 times fresh media is added to the cell pellet.

The following examples by way of illustration and not limitation, further define the present invention.

EXAMPLE 1

Freezing media

Chee's Essential Medium (CEM) supplemented with:

10 ml FBS per 90 ml CEM 10 ml DMSO per 90 ml CEM 0.584 g Glutamine per Liter CEM 10 mU Insulin per ml CEM $10^{-6}$ M Dexamethasone 50 ug Gentamicin per niL CEM

EXAMPLE 2

Filling method

Prior to filling into a bag or a tube, the cell suspension was maintained in a pre-chilled sterile bottle. The suspension was continuously swirled in order to keep the cell density consistent.

When Cryocyte Bags trademark of Baxter for plastic bags, were filled, the roller clamps of the y-connection were clamped shut. The bags were pre-chilled to 2–8 degrees Celsius for about 30 minutes prior to use. The plunger was aseptically removed from a 60 cc syringe, the syringe barrel was secured into the luer lock fitting of the y connection tubing, and 50 ml of hepatocyte cryo-suspension was aseptically poured into the syringe barrel. Thereafter the inlet tubing clamp was opened and the cell suspension was allowed to flow into the bag by gravity. The bag was then gently compressed until a stream of cells was observed flowing up into the inlet tubing to remove all the excess air from the bag. Thereafter, the compression was removed until the cells re-entered the bag and the y connection was clamped shut as soon as air was observed re-entering the bag. Lastly, the y connection tubing was sealed shut using a heat sealer and excess tubing was removed.

EXAMPLE 3

Non-control rate freezer method

Cryocyte bags trademark of Baxter for plastic bags, or tubes filled in a accordance with Example 2 were placed in a ½ inch thick styrofoam box. Either cryocontainer was then placed in an ultra-low temperature freezer set to minus 70 degrees Celsius and kept there for about 2 to 2½ hours. The cryocontainers were then removed from the freezer and immediately quenched in liquid nitrogen and placed in long term storage. The cryopreservation cycle is monitored and documented via a Kaye Portable Validator during long term storage.

EXAMPLE 4

Control rate freezer method

Cryocyte bags filled with cells were sandwiched between custom aluminum freezing plates. They were then placed in a chamber of a control rate freezer programmed with the following freezing profile. Cells were slowly cooled to 4 degrees Celsius at a rate of 1 degrees Celsius/minute. Thereafter, the cooling rate was changed to 2.5 degrees Celsius/minute until the a temperature of minus 12 degrees Celsius was reached, the point of release of latent heat. The released latent heat was compensated for by dropping the chamber's temperature 25 degrees/minute until the temperature fell to minus 70 degrees Celsius. At that point, the chamber's temperature was immediately increased to minus 20 degrees Celsius, at a rate of 15 degrees Celsius/minute. A freezing rates of 1.5 degrees Celsius/ minute was then utilized to reach the final freezing temperature of minus 70 degrees Celsius. Once this temperature was obtained, the cryopreserved cells were removed from the control rate freezer and placed in vapor phase nitrogen for 10–24 hours. Thereafter, they were placed directly in liquid nitrogen for long term storage.

The freezing cycle's chamber and sample temperature are documented with NIST (National Institute of Science and Technology) thermocouples.

Hepatocytes cryopreserved via the aforementioned general and specific guidelines typically showed 80–99% of the initial viability and 50–80% of the metabolic activity of fresh cells. These results are illustrated by the data in the following tables.

TABLE 1

Viability and Diazepam Metabolic Activity of Fresh and Cryopreserved Hepatocytes

| Sample | % Viability | Diazepam Metabolic Activity (ug/$10^6$ cells/hr) |
|---|---|---|
| Fresh Cells | | |
| 1 | 80 | 7.5 |
| 2 | 92 | 7.8 |
| 3 | 88 | 5.8 |
| Cryopreserved Cells | | |
| 1 | 70 | 5.9 |
| 2 | 81 | 4.5 |
| 3 | 85 | 4.1 |
| % of Fresh Cells | | |
| 1 | 88 | 79 |
| 2 | 88 | 58 |
| 3 | 97 | 71 | wherein:

Fresh Cell=freshly isolated/cultured porcine hepatocytes

Cryopreserved Cells=porcine hepatocytes which have been cryopreserved, stored in liquid nitrogen and thawed.

Viability=assessed by trypan blue exclusion assay

Diazepam Metabolic Activity=metabolite production

By way of recapitulation the present invention discloses a novel artificial liver support device comprising novel cryopreserved hepatocytes produced by the novel cryopreservation process comprising isolating hepatocytes, preparing a cryoprotective medium, suspending liver cells into said medium, dispensing said hepatocytes into freezer safe containers, freezing said containers for a particular period of time under particular conditions, nitrogen storing said containers if long term storage is desired and thawing said cells when ready for use. Thus cryopreserved cells demonstrate 80–99% viability and a 50–80% metabolic activity of fresh cells making them very desirable for use in hybrid ALS devices or as the basis for hepatocyte transplantation. As bioartificial livers they can bridge hepatic function until a donor liver becomes available for transplantation or until the patient's liver regenerates itself.

Since certain changes may be made without departing from the scope of the invention as described herein, it is intended that all matter described in the foregoing specification, including the examples, shall be interpreted as illustrative and not in a limiting sense.

We claim:

1. An artificial liver support system comprising cryopreserved hepatocytes having an initial viability of 80–99% and having 50–80% of the metabolic activity of fresh cells.

2. The artificial liver support system of claim 1, wherein the cryopreserved hepatocytes have 50–80% diazepam metabolic activity.

3. An artificial liver comprising a liver support device comprising cryopreserved hepatocytes having an initial viability of 80–90% and 50–80% of the metabolic activity of fresh cells.

4. The artificial liver of claim 3, wherein the liver support device comprises micro carriers, flat sheet membranes, hollow fibers, packed beds of gel, fluidized beds or stir tanks.

5. An artificial liver comprising a liver support device comprising cryopreserved primate or porcine hepatocytes cryopreserved by the process comprising the steps of:
   a. dispensing hepatocytes into freezing containers;
   b. freezing said containers from between minus 50 to minus 90 degrees Celsius;
   c. storing said containers in liquid or vapor nitrogen;
   d. thawing said cryopreserved hepatocytes when ready for use; and
   e. removing residual cryoprotectant media.

6. The artificial liver of claim 5, further comprising the step of preparing a cryoprotective medium and suspending hepatocytes in said medium prior to dispensing said hepatocytes into freezing containers.

7. The artificial liver of claim 6, wherein the cryoprotectant is DMSO, polyethylene glycol, amino acids or propanediol.

8. The artificial liver of claim 6, wherein the hepatocyte culture media is Chee's Essential Media, Modified Eagle Media, Dulbecco's Modified Eagle Medium, Leibowitz, Waymouth, or Kreb's media.

9. The artificial liver of claim 6, wherein the hepatocyte culture media is Chee's Essential Media supplemented with thymidine, arginine, insulin, dexamethasone, glutamine and mammalian serum.

10. The artificial liver of claim 9, wherein the mammalian serum comprises fetal bovine serum, fetal calf serum and/or porcine serum.

11. The artificial liver of claim 10, wherein the mammalian serum comprises fetal bovine serum, fetal calf serum and/or porcine serum in concentrations ranging from 10–90%.

12. The artificial liver of claim 9, wherein the hepatocyte culture media is further supplemented with DMSO ranging from about 10 to about 15%, albumin ranging from about 3.5 to about 15% and glycerol ranging from about 10 to about 20%.

13. The artificial liver of claim 6, wherein the hepatocyte culture media is Chee's Essential Media supplemented with 5–20% fetal bovine serum and 5–15% dimethyl sulfoxide.

14. The artificial liver of claim 5, wherein the freezing containers comprise vials, bags or canes.

15. The artificial liver of claim 5, wherein the cryopreserved hepatocyte density within said freezing containers is from about 5 to about $40 \times 10^6$ cells/ml.

16. The artificial liver of claim 5, wherein said freezing containers are sandwiched between freezing plates.

17. The artificial liver of in claim 16, wherein the freezing plates are separated by spacer means.

18. The artificial liver of claim 5, further comprising the step of seeding the hepatocytes after they have been cooled below freezing.

19. The artificial liver of claim 18, wherein seeding is accomplished by inserting a cold metal rod into said freezing containers.

20. The artificial liver of claim 18, wherein seeding is accomplished by introducing a blast of liquid nitrogen into said freezing containers.

21. The artificial liver of claim 5, wherein the freezer is a control rate freezer.

22. The artificial liver of claim 21, wherein the control rate freezer is programmed as follows:
   a. start when the sample's temperature reaches minus 4 degrees
   b. cooling rate between 1–10 degrees Celsius per minute before the release of latent heat(minus 12 degrees Celsius).
   c. during the latent heat release, drop the chamber temperature to a rate of 25 degrees Celsius per minute until the temperature falls between minus 60 and minus 70 degrees Celsius then increase the chamber's temperature immediately to between minus 12 and minus 20 degrees Celsius at a rate of 15 degrees Celsius per minute.
   d. Continue freezing thereafter at freezing rates between 1–10 degrees Celsius per minute until a final freezing temperature between minus 50 and minus 90 degrees Celsius is reached.

23. The artificial liver of claim 22, wherein the latent heat release is compensated for with a blast of nitrogen.

24. The artificial liver of claim 22, wherein the control rate freezer further comprises a validator.

25. The artificial liver of claim 5, wherein the hepatocytes are stored at temperatures below −120° Celsius.

26. The artificial liver of claim 5, wherein the hepatocytes are thawed via a 37°–42° Celsius bath.

27. The artificial liver of claim 26, wherein the cells are removed from the bath when a slush appears and then poured into a centrifuge tube containing cold culture media.

28. The artificial liver of claim 27, wherein the initial cell suspension volume in the centrifuge tube is diluted by adding 5 to 10 times the initial cell volume in fresh cold culture media.

29. The artificial liver of claim 28, wherein the suspension is then spun down at 7–15 g for 2–5 minutes.

30. The artificial liver of claim 29, wherein residual DMSO is removed.

31. The artificial liver described in claim 30, wherein about 2 to about 4 times fresh media is added to the cell suspension.

* * * * *